United States Patent [19]

Gordy

[11] Patent Number: 4,815,218
[45] Date of Patent: Mar. 28, 1989

[54] GAUGE FOR CALIBRATING SURGICAL SCALPEL

[75] Inventor: Walker L. Gordy, Corona, Calif.

[73] Assignee: Cilco, Inc., Bellevue, Wash.

[21] Appl. No.: 72,912

[22] Filed: Jul. 14, 1987

Related U.S. Application Data

[62] Division of Ser. No. 873,951, Jun. 13, 1986, Pat. No. 4,730,613.

[51] Int. Cl.⁴ ............................................. B27G 23/00
[52] U.S. Cl. ...................................... 33/628; 33/201; 128/305
[58] Field of Search .......... 128/305; 33/169 R, 169 B, 33/169 F, 628, 168 R, 168 B, 143 E, 162, 201

[56] References Cited

U.S. PATENT DOCUMENTS

| | | | |
|---|---|---|---|
| 4,538,356 | 9/1985 | Knepshield et al. | 33/628 |
| 4,630,378 | 12/1986 | Kulp et al. | 33/628 |
| 4,662,075 | 5/1987 | Mastel et al. | 33/628 |

Primary Examiner—Harry N. Haroian
Attorney, Agent, or Firm—Pravel, Gambrell, Hewitt, Kimball & Krieger

[57] ABSTRACT

A surgical scalpel having an extendable blade, said blade being extended by rotating a movable portion of a barrel with respect to a fixed barrel portion, the initial extension being done at a fast rate and the final extension or depth adjustment being done at a slow rate. Additionally, the invention includes a gauge in combination with the scalpel for calibrating blade depth, the gauge consisting of a base, a slidable block with a tapered ridge and width markings and a slidable support for the scalpel, so that the scalpel can be abutted with the block for measurement and backed off for block adjustment.

3 Claims, 4 Drawing Sheets

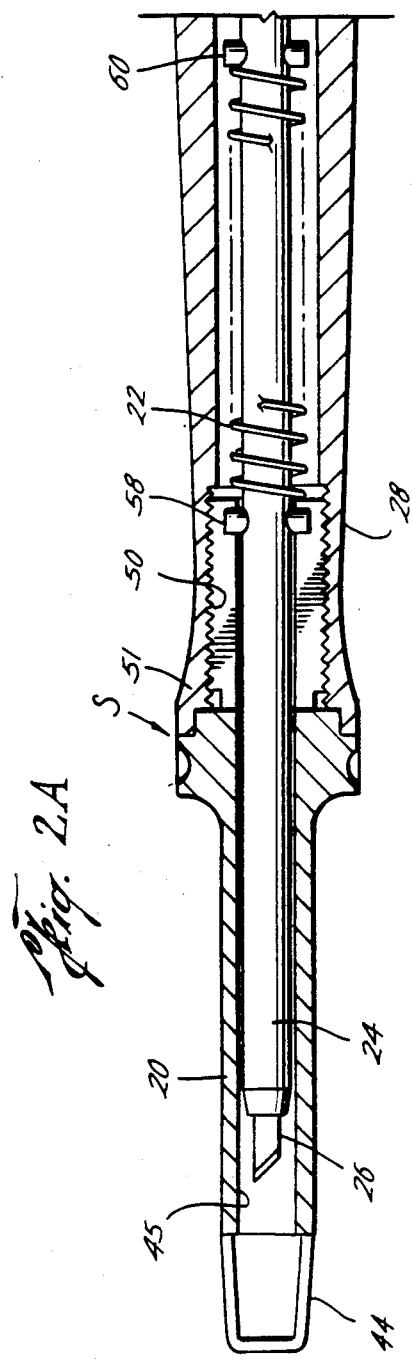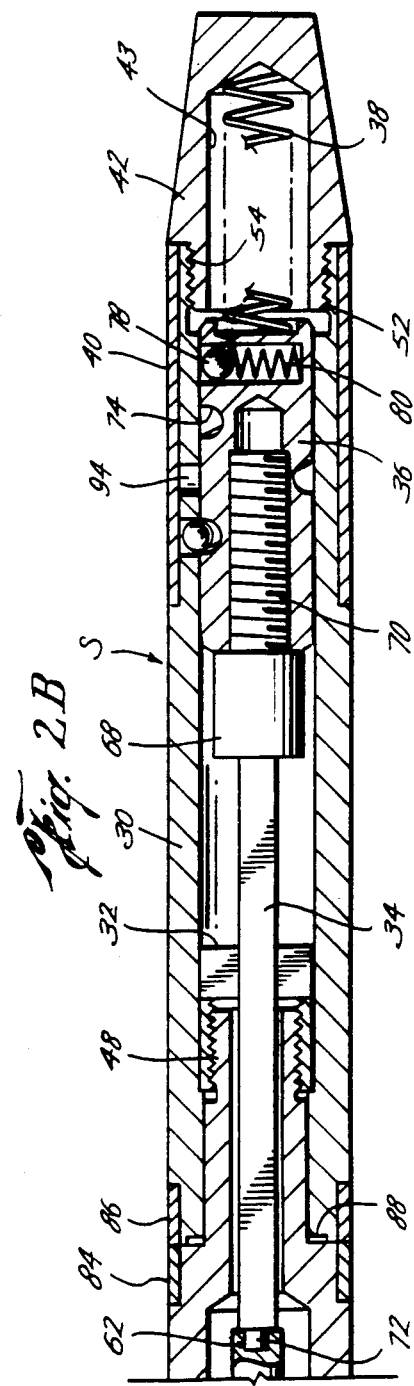

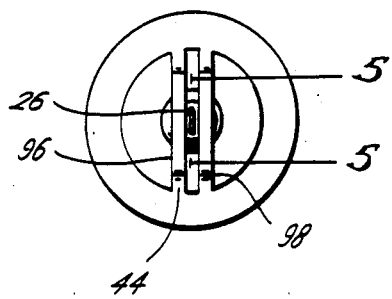
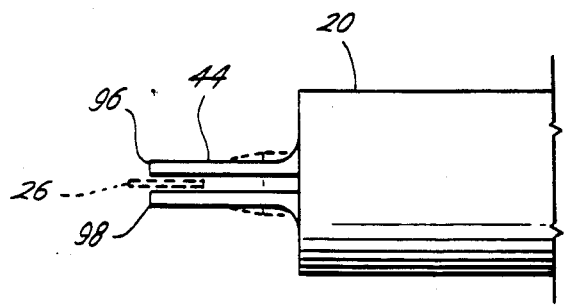
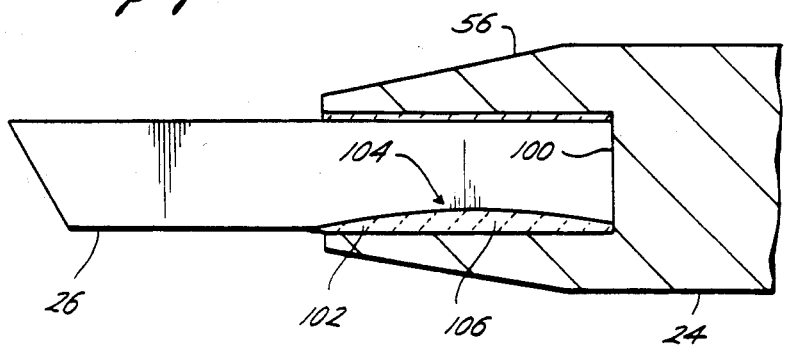
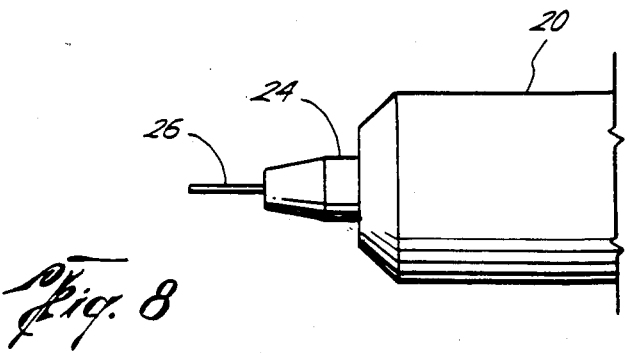

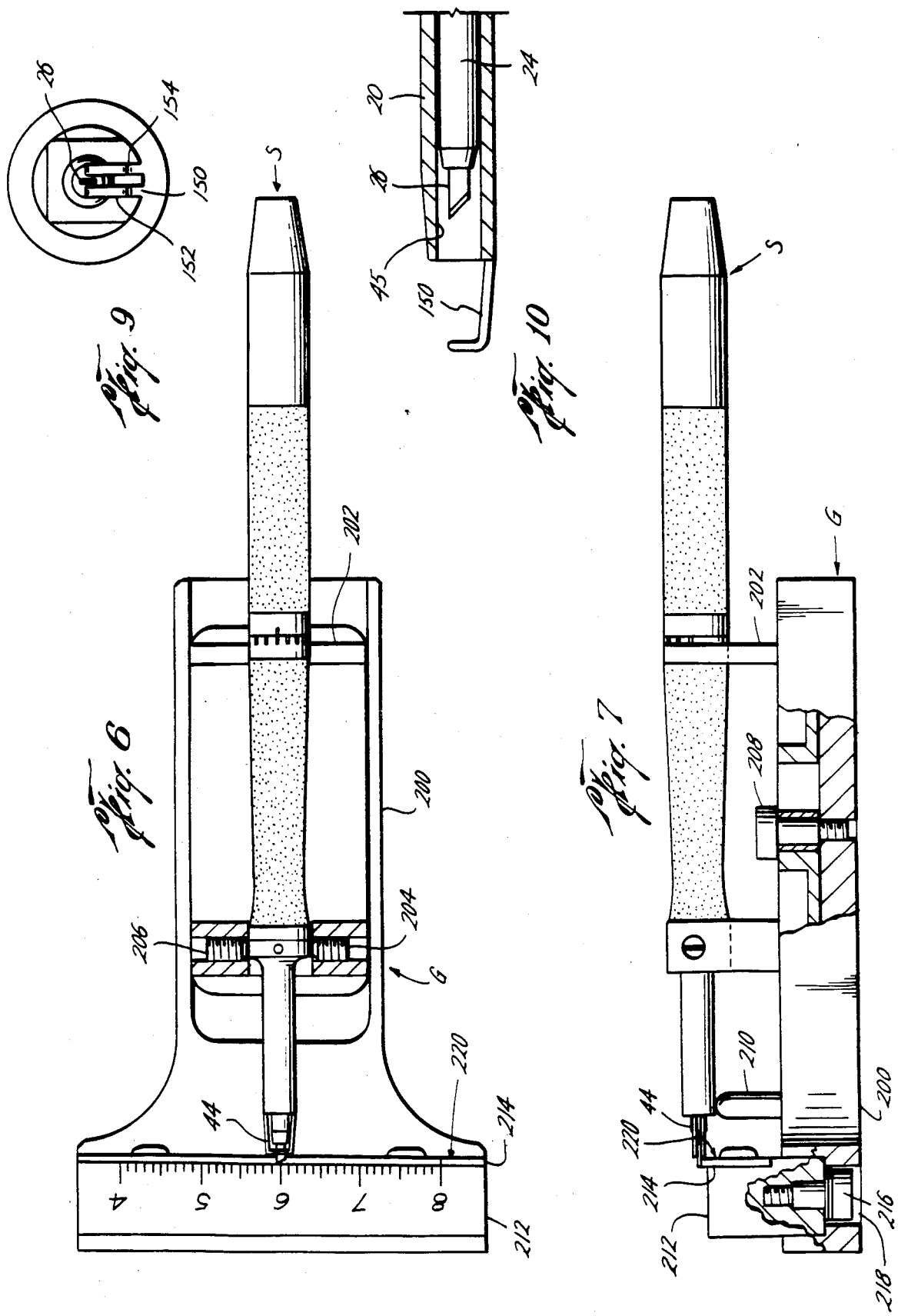

4,815,218

GAUGE FOR CALIBRATING SURGICAL SCALPEL

This is a division of application Ser. No. 873,951, filed June 13, 1986, now U.S. Pat. No. 4,730,613.

BACKGROUND OF THE INVENTION

1. Field of the Invention

The present invention relates to the field of medical instruments and more particularly to a surgical scalpel having an adjustable depth of cut.

2. Description of the Prior Art

Scalpels having adjustable depths of cut are used in many types of surgical procedures. In particular, an adjustable depth scalpel is useful in performing a surgical procedure known as radial keratotomy where radial cuts are formed in the outer surface of the eyeball. This procedure changes the curvature of the eyeball and alleviates the symptoms of myopia. Examples of scalpels designed to cut at adjustable depths are shown in U.S. Pat. Nos. 4,499,898 and 4,516,575.

Such a scalpel should allow a variable adjustment of the projection distance of the blade over a relatively wide range and include a convenient means for retracting and extending the blade. The retracted position is provided for protecting the blade when it is not in use while the variable adjustment is provided to control the depth of the incision.

It is desirable that the motions required to perform the extension, retraction and depth adjustment be simple and not allow unsatisfactory tolerances or movement of the blade to occur during use. To this end it is desirable that only one portion of the scalpel be required to turn or move to provide both the extension/retraction and variable depth functions. Prior art devices provide both extension/retraction and depth adjustment, but use combinations of movements and different scalpel portions to provide the respective extension/retraction or depth adjustment and control.

It is also desirable that the scalpel have a surface that provides maximum tactile feedback to the surgeon, allowing more accurate incisions to be made. The scalpel should also have a mechanism for maintaining a uniform depth of cut and yet allow maximum visibility of the knife blade at all times. The blade should also be firmly attached to the blade holder to prevent any inaccuracies due to blade wobble.

The incision depth is critical in many of the procedures using adjustable scalpels. Gauges to accurately set the blade depth in very fine graduations have been developed, as shown in U.S. Pat. No. 4,538,356. In the disclosed gauge, the scalpel is fixed in place and the disk rotated to align the depth marks with the blade. This gauge has the problem that the scalpel foot, the resting surface of the scalpel contacting the tissue, is in contact with the disk. When the disk is rotated, the two metal surfaces rub and an uneven finish appears on the foot, leading to possible scratches when the scalpel is used to make an incision.

SUMMARY OF THE INVENTION

The present invention is directed to a scalpel that includes these features and provides advantages over known devices. The scalpel includes a multiple piece barrel or body, one portion of which is able to rotate while another portion is fixed. A blade holder is provided to hold the blade and cooperate with an adjustment mechanism for reciprocating the blade holder relative to the barrel so that the blade can be extended and retracted.

A portion of the blade holder is inserted into a stationary portion of the barrel and biased in a retracted position by a spring. A barrel portion containing a foot that is designed to protect the blade and provide a base for controlling the depth of cut is fixedly connected to the stationary barrel. A rear portion of the blade holder includes a fine pitch screw thread for setting the depth of cut. A piece that includes a second fine pitch thread designed to cooperate with the threads on the blade holder also includes at its other end a coarse pitch thread. The latter threads operate with an engagment means located on the inside surface of the movable portion of the barrel. The rear portion of the blade holder is rotatably mated with the front portion of the blade holder and the movable barrel portion is rotatably connected to the stationary barrel portion.

By turning the movable barrel portion and holding the stationary portion the blade is extended by the action of the coarse threads. The dual threaded piece is then locked in position with the movable barrel portion by means of a ball and spring mechanism. Further turning of the movable barrel portion provides the infinitely variable adjustment of the blade projection depth due to the action of the fine threads. Retraction of the blade is done by adjusting the blade projection to the minimum distance and then turning the movable barrel portion to release the ball and spring and allow the coarse threads to cause the blade holder to retract, thereby protecting the blade.

The foot used to provide the resting surface of the scalpel is trapezoidal in shape, having dimensions greater than the blade, allowing the blade to easily be seen during an incision and yet allowing a firm and stable resting surface.

The blade is held in place in the blade holder by mechanical action due to the shape of the blade portion inserted into the blade holder. The blade contains a concave or recessed portion in the inserted portion. The blade is inserted into the blade holder, which provides a loose fit. Solder is then flowed into the remaining volume between the blade holder and the blade. The solder provides a tight seal and the concave portion of the blade prevents the blade from moving relative to the blade holder.

The invention includes a gauge for use with the scalpel to allow the blade depth to be accurately set. The gauge has a base, a stand and a calibrated block. The scalpel is placed in a stand that can move longitudinally. The block has a tapered ridge with corresponding thickness markings to allow the blade depth to be set. The block moves transversely, allowing the varying thicknesses to be aligned under the scalpel blade. The scalpel can be moved away from the block, the block adjusted and the scalpel brought back into contact with the block. In this manner, the blade depth can be adjusted without having the block and the scalpel foot rubbing and creating an uneven surface.

BRIEF DESCRIPTION OF THE DRAWINGS

A better understanding of the present invention can be obtained when the detailed description of exemplary embodiments set forth below is considered in conjunction with the accompanying drawings, in which:

FIGS. 2A and 2B are partial sectional views of the scalpel of FIG. 1, with the scalpel blade in its retracted position;

FIG. 3 is a plan end view of the scalpel of FIG. 2A, looking along the line 3—3 of FIG. 2A;

FIG. 4 is a plan view of the scalpel of FIG. 2A looking along the new line 4—4 of FIG. 2A, with the broken lines showing the scalpel blade in its extended position;

FIG. 5 is a partial sectional view of the scalpel of FIG. 3 looking along view 5—5 of FIG. 3;

FIG. 6 is a top plan view of the scalpel of FIG. 1, showing its position on a depth gauge for adjusting the scalpel blade;

FIG. 7 is a side plan view of the scalpel and gauge of FIG. 6 with the depth gauge shown partially in section looking along the new lines 7—7 of FIG. 6;

FIG. 8 is a top plan view of a scalpel blade and holder without a protective foot;

FIG. 9 is a plan end view of scalpel having an alternative protective foot; and

FIG. 10 is a partial sectional view of the scalpel of FIG. 9, with the blade in its retracted position.

DETAILED DESCRIPTION OF THE EXEMPLARY EMBODIMENTS

Figure 1:
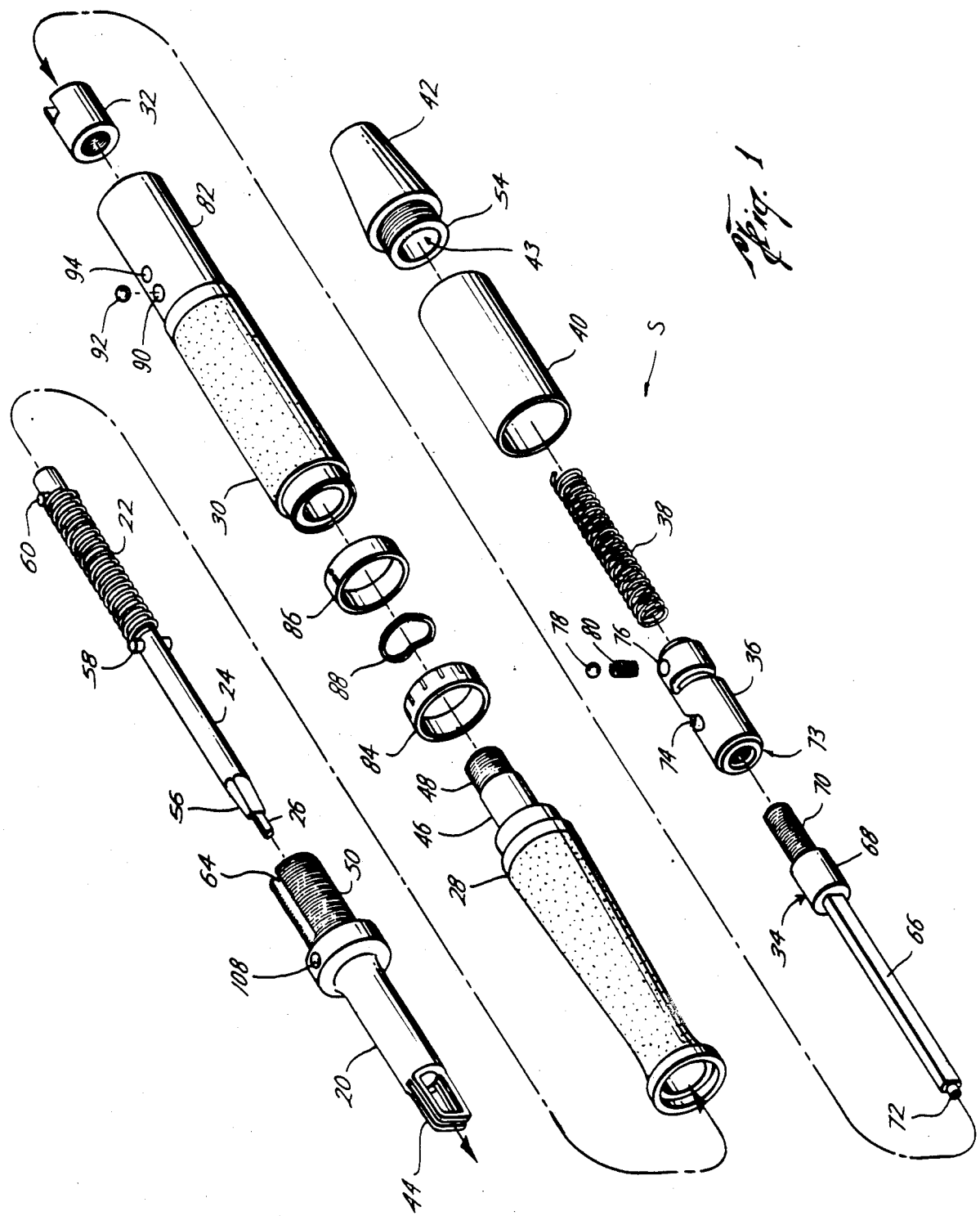
FIG. 1 is an exploded isometric view of a scalpel according to the present invention.

Referring to FIGS. 1, 2A, and 2B, the surgical scalpel of the present invention is designated generally by reference letter S. The main structural portions of the scalpel S include a barrel nose 20, a first spring 22, a blade holder 24 for holding a blade 26, a fixed or stationary barrel 28, a movable barrel 30, a nut 32, a threaded blade holder end piece 34, a dual threaded insert 36, a second spring 38, a sleeve 40 and a barrel end 42.

The scalpel S is generally cyindrical in shape, with the fixed barrel 28 being slightly tapered to better conform to the fingers of the user when gripped. The barrel nose 20 includes a foot 44 at the outer end and has an axial bore 45 with a diameter that is slightly larger than the diameter of the blade holder 24 to provide a snug fit. The barrel nose 20 has a threaded portion 50 that cooperates with a threaded portion 51 at one end of the fixed barrel 28. The threaded portion 50 contains longitudinal grooves 64 that receive pins 58 on the blade holder 24 for preventing it from rotating relative to the barrel 28 as the blade 26 is extended and retracted, as described in greater detail below.

The barrel 28 is generally hollow and cylindrical in shape, with a reduced diameter shank 46 that includes threads 48 at the end opposite the blade 26 or outer end. The shank 46 is of a reduced diameter to fit inside the movable barrel 30, which is also hollow and cylindrical in shape, having internal threads 52 and a reduced diameter portion 82 at the outer end. The barrel end 42 is shaped generally as a truncated cone with an internal bore 43, and external threads 54 shaped and dimensioned to cooperate with the threads 52 of the movable barrel 30.

Preferably, as shown in FIG. 1, the outer surfaces of the barrel pieces have a brushed or turned surface instead of knurls because it has been determined that knurls actually desensitize a physician's fingers, decreasing the sensitivity of the fingers to minute changes in blade drag, angle and position while making an incision. The brushed surface does not reduce the grip on the scalpel S and the brushed surface increases the tactile feedback to the physician.

The blade holder 24, designed to fit inside the barrel nose 20 and barrel 28, is generally cylindrical in shape and has a frustum 56 at the blade end, a first transversely mounted pin 58 located approximately at the center of the blade holder 24 and a second transversely mounted pin 60 near the outer end, which end also contains a hole 62 that mates with the blade holder end piece 34. A spring 22 is mounted coaxially with the blade holder 24 and located between the transverse pins 56, 60. The blade holder end piece 34 comprises a cylindrical portion 72 that mates with the hole 62, a rectangular portion 66, a cylindrical portion 68 and an externally threaded cylinder 70. The threads on the cylinder 70 are preferably left-handed for reasons described in greater detail below.

The dual threaded insert 36 is generally cylindrical in shape and contains a threaded bore 73 that mates with the threaded cylinder 70 of the holder end piece 34. The insert 36 also contains an external spiral groove 74 that operates as a thread to allow the coarse, rapid movement of the blade 26. Additionally, the insert 36 contains a transverse bore 76 that is perpendicular to the longitudinal axis of the insert 36. The bore 76 contains a ball 78 and a spring 80 for providing a positive locking action that causes a changeover from coarse to fine movement of the blade 26.

The blade 26 is preferably formed of an industrial diamond known for its durability. The threaded insert 34 is preferably formed of a nickel-bronze alloy, with the foot 44 and the blade holder portions formed of type 303 stainless steel. The barrel portions are preferably formed of a titanium alloy.

Assembly of the scalpel S is accomplished by sliding a pair of rings 84 and 86 onto the fixed barrel 28 and the movable barrel 30 respectively. Visible notches on ring 84 and a single notch on ring 86 act as references to determine whether the blade depth has been altered after the blade is set at the desired depth. After a wave washer 88 is placed over the fixed barrel shank 46, the two barrel portions 28 and 30 are mated together with the shank 46 located inside the movable barrel 30. A nut 32 having a partially rectangular longitudinal bore approximately the size of the rectangular barrel end portion 66 and a remaining bore threaded to mate with threads 48 is then inserted inside the movable barrel 30, mated with threads 48 and tightened sufficiently to slightly compress the washer 88 and yet allow the movable barrel 30 to rotate with respect to the fixed barrel 28.

The blade holder end piece 34 is fully threaded into the dual threaded insert 36. The ball 78 and spring 80 are inserted in the bore 76 of the insert 36 and the assembly is slid into the barrel assembly until the groove 74 is located under a hole 90 in the movable barrel 30. A ball 92 is inserted in the hole 90 and the underlying groove 74. The sleeve 40 is positioned around the movable barrel 30 to restrain the ball 92. The spring 38 is then placed in the bore 43 of the barrel end 42, which in turn is threaded into the movable barrel 30.

The blade holder 24 with the spring 22 previously installed is slid into the barrel nose 20, taking care not to damage the blade 26. This assembly is then screwed into the fixed barrel 28 and the barrel nose 20 and barrel end 42 are overtorqued to prevent accidental disassembly of the scalpel S.

The blade 26 is extended, retracted or depth adjusted by turning the movable barrel 30 relative to the fixed barrel 28. The blade 26 moves outwardly towards its extended position as the movable barrel 30 is rotated in a normal right-hand manner because the holder end 34 cannot rotate axially, being restrained by the nut 32. This restraint causes the groove 74 to spiral along the ball 92. Because the insert 36 is fully threaded onto the holder end piece 34 creating a higher friction joint, the insert 36 does not rotate relative to the holder end piece 34, and because the movable barrel 30 cannot move longitudinally with respect to the fixed barrel 28 due to the nut 32, the insert 36 moves longitudinally, pushing the holder end piece 34 and the blade holder 24 out the barrel, thereby extending the blade 26 to the cutting position. The coarse pitch of the acting threads causes the blade 26 to extend at a relatively rapid rate. After the insert 36 has moved longitudinally a sufficient distance, the ball 78 pops into a hole 94 that is located in the movable barrel 30.

This movement of the ball 78 into the hole 94 indicates that the coarse movement of the extension is completed and the fine depth adjustment can be performed. Further right-hand rotation of the movable barrel 30 causes the fine pitched left-handed threads of the insert 36 and the holder end piece 34 to unthread and move the blade 26 out a small distance for each movable holder 30 rotation. This is the slow travel portion of the blade 26 adjustment procedure. This movement occurs because there is less resistance to movement at this joint then at the now higher resistance coarse thread joint due to the added resistance or lockingaction of the ball 78 and spring 80. The fine pitch of the threads allows the amount of the blade 26 extending beyond the foot 44 to be precisely set to the desired distance using an appropriate depth gauge. The spring 38 maintains the holder end piece 34 and the blade holder 24 in contact, removing play between these two parts and keeping the extended depth constant. The blade is set to the desired depth and the incisions made.

After making the incisions the blade 26 is retracted for protection. This is done by turning the movable barrel 30 in the opposite direction (counterclockwise when viewed from the barrel end 42). First the blade depth is reduced to the minimum by the action of the fine threads. The holder end piece 34 is then fully screwed into the insert 36 and cannot move any further, resulting in a high resistance to further rotation at this joint. The resistance becomes great enough that the resistance to turning of the coarse thread as supplemented by the ball 78 is overcome, causing the holder end piece 34 to retract into the barrel. The blade holder 26 is retracted at the same time as the holder end piece 34 due to the bias of spring 22. When the ball 92 reaches the end of the groove 74, the blade 26 is fully retracted and no further rotation of the movable barrel 30 is possible, indicating full retraction.

The extension, retraction and depth adjustment of the blade 26 is performed by the rotation in one direction of only the movable barrel 30. This is a simple movement that does not require the surgeon to perform a combination of movements or use different portions of the scalpel to extend or retract the blade or set the blade depth. This ease of use simplifies the surgeon's task, increasing his accuracy, reliability and confidence.

The foot 44 is generally trapezoidal shape (see FIGS. 1 and 2A) and rests on the tissue being cut to provide a stable reference so that the blade cutting depth does not vary because of a bulk longitudinal movement of the scalpel S. The shape of the foot 44 allows a relatively large portion of the blade 26 to be visible from different angles. The trapezoidal shape also allows protection of the delicate blade 26, which is vulnerable to transverse forces and therefore increases the life of the scalpel S.

FIGS. 3 and 4 show additional views of the foot 44 to illustrate that the foo 44 is formed of two parallel elements 96 and 98, both having trapezoidal shapes. The two elements are necessary to allow space for the blade 26 to extend between the elements and yet provide blade protection on both sides.

FIGS. 9 and 10 show views of an alternative foot 150 to illustrate that the foot 150 is formed of two parallel elements 152 and 154, both having partially trapezoidal shapes, essentially portions of the elements 96 and 98 of the previous foot 44.

FIG. 8 shows an embodiment of the scalpel S without a foot 44. This embodiment is used for surgical purposes not requiring a stable platform of the foot 44. The extension and retraction features would be retained in this embodiment of the scalpel S to protect the blade when not in use, but the infinitely variable features could be removed to lower the unit cost.

FIG. 5 illustrates a preferred connection between the blade 26 and the blade holder 24. The blade holder 24 has a slot 100 that is approximately the shape of the blade 26 cut into the frustum 56. The blade 26 is formed with a concave or recessed portion 104 (shown greatly exaggerated in FIG. 5) along one side on the end inserted into the slot 100. When the blade 26 has been inserted into the slot 100 and properly aligned, solder 102 is flowed into the gaps between the blade 26 and the blade holder 24 for holding the blade 26 in place on the slot 100. This fixation method has advantage over a typical friction fit that tends to have many gaps, thereby decreasing the resisting surface area and increasing the possibility of blade breakage during insertion.

The solder is preferably a white gold material having approximately 35% silver, 45% gold and 15-20% copper with a flowing temperature around 800° F. The recess 104 in the blade 26 results in a solder bump 106 after the solder 102 has hardened. This bump 106 increases the resistance of the blade 26 to movement relative to the blade holder 24 by supplementing the friction forces which have been increased due to the complete coverage by the solder 102. The supplemental resistance occurs because it is necessary to grossly deform either the solder 102 or the blade 26 to allow the blade 26 to wiggle. This increases the stability of the blade 26, improving the resulting incision or increasing the length of time needed between repairs due to blade wobble.

FIGS. 6 and 7 show a gauge G that can be used to calibrate and set the blade extension of the scalpel S. The gauge G has three main elements: a base 200, a stand 202 and a block 212. The base 200 provides a stable base for properly locating all the elements and providing an accurate depth adjustment. The scalpel S is placed on the stand 202 with the plane of the foot 44 parallel with the plane of the base 200. In the preferred embodiment, this places a recess 108 and an opposite recess (not shown) parallel with the base 200 to allow corresponding ball and spring mechanisms 204 and 206 to lock the scalpel S to the stand 202. After the scalpel S is attached to the stand 202, the foot 44 is brought into contact with face 220 of a block 212. This face of the block is the zero depth face and is the reference used to measure blade extension. The stand 202 and the foot 44 are maintained against the face 220 by manual pressure. A pin 208 is used to keep the stand 202 from rocking if one end of the scalpel S is pressed while mounted in the stand 202. A post 210 provides further support and protection against accidental rocking while the blade 26 is extended by contacting the barrel nose 20.

After the scalpel S is in place, the block 212 can be slid back and forth until the desired depth mark is located by the blade 26. The block 212 is restrained to allow only perpendicular motion by screws 216 located in the base 200 and corresponding slot 218 for the screw heads located in the block 212. The block 212 contains a ridge 214 located adjacent face 220 with a varying thickness from one end of the block 212 to the other. The thickness of the ridge 214 is marked on the upper surface of block 212 to allow the proper thickness to be placed next to the blade 26 to allow the blade 26 to extend the desired distance beyond the foot 44. By giving the ridge 214 a shallow taper it is possible to set the blade depth accurately in the fine increments necessary for the desired surgical procedures. The blade 26 is extended until the desired reference location on the blade 26 passes the roidge 214. Because the stand 202 can move longitudinally, the foot 44 can be removed from contact with the block 212 as the block 212 is moved transversely. In this manner, scratching and abrasion of the foot 44 can be avoided, extending the life of the scalpel S and reducing the number of scratches made to the patient. After setting the blade depth using the gauge G, the scalpel S is ready for use.

The foregoing disclosure and description of the invention are illustrative and explanatory of the invention and various changes in the size, shape and materials, as well as in the details of the illustrated construction may be made without departing from the spirit of the invention, all of which are contemplated as falling within the scope of the appended claims.

I claim:

1. A gauge for measuring the projection of a blade-like flat member from an elongated body associated therewith, the body having an axia along which the flat member projects and a front surface from which the member projects a distance to be measured, comprising:

a base;

means for holding the body, said holding means mounted on said base and movable between a first and a second position; and means for indicating the member projection, said indicating means mounted on said base, having markings indicative of the member projection and movable relative to said holding means to align a desired marking with the projected member, said indicating means abutting the body front surface when said holding means is in the first position and said indicating means displaced from the body front surface when said holding means is in the second position, wherein said indicator means comprises a block having a tapered ridge and markings indicative of the width of the ridge, wherein said block is movable perpendicularly to the member projection axis and wherein said ridge abuts the body front surface when said holding means is in the first position, and wherein said holding means is adapted to be movable while the member projection is being measured.

2. The gauge of claim 1, wherein said holding means includes two axially displaced supports, at least one of the supports being shaped to matingly engage a correspondingly shaped locating means on the outer surface of the body at a predetermined axial position thereof, the shaped support and locating means being adapted by mutual engagement thereof to retain the body in a predetermined axial position.

3. The gauge of claim 2, wherein the locating means comprises a pair of circular recesses in the body at a predetermined axial position on opposite sides of the body and the shaped support comprises a plate with a U-shaped cutout, having biased projections on the sides of the cutout corresponding with the recesses.

* * * * *